United States Patent

Pearson et al.

[11] Patent Number: 5,916,779
[45] Date of Patent: Jun. 29, 1999

[54] STRAND DISPLACEMENT AMPLIFICATION OF RNA TARGETS

[75] Inventors: Robert E. Pearson, Durham; Julie A. Dickson, Raleigh, both of N.C.; Majid Mehrpouyan, San Jose, Calif.

[73] Assignee: Becton, Dickinson and Company, Franklin Lakes, N.J.

[21] Appl. No.: 08/854,041

[22] Filed: May 8, 1997

Related U.S. Application Data

[63] Continuation-in-part of application No. 08/531,986, Sep. 21, 1995, abandoned.

[51] Int. Cl.$^6$ .............................. C12P 19/34; C07H 21/00
[52] U.S. Cl. .......................... 435/91.2; 435/91.1; 435/6; 536/24.33
[58] Field of Search .................................. 435/91.2, 91.1, 435/91.5, 91.51, 6; 536/24.31, 24.33

[56] References Cited

U.S. PATENT DOCUMENTS

| | | | |
|---|---|---|---|
| 5,270,184 | 12/1993 | Walker et al. | 435/91.2 |
| 5,322,770 | 6/1994 | Gelfand | 435/6 |
| 5,455,166 | 10/1995 | Walker | 435/91.2 |
| 5,523,204 | 6/1996 | Singer et al. | 435/5 |
| 5,631,147 | 5/1997 | Lohman et al. | 435/91.2 |

FOREIGN PATENT DOCUMENTS 0 632 134 A2  1/1995  European Pat. Off. .

OTHER PUBLICATIONS

J. W. Larrick "Message Amplification Phenotyping (MAPping)—principles, practice and potential" *Trends Biotech* 10:146–152 (1992).

Dickson et al. Abstracts of the General Meeting of the American Society for Microbiology 96. 1996. 28.

*Primary Examiner*—Kenneth R. Horlick
*Assistant Examiner*—Jeffrey Siew
*Attorney, Agent, or Firm*—Donna R. Fugit

[57] ABSTRACT

Strand Displacement Amplification has been adapted to reverse transcription amplification of RNA targets. The method of the invention is referred to as reverse transcription SDA (rtSDA) and may be performed as a two-step process or as a one-step process in which cDNA copies of an RNA target sequence are generated and amplified concurrently. In the one-step process, rtSDA reaction conditions are such that a conventional reverse transcriptase and a DNA-dependent polymerase function together in a single reaction to produce cDNA and amplify it.

19 Claims, 1 Drawing Sheet

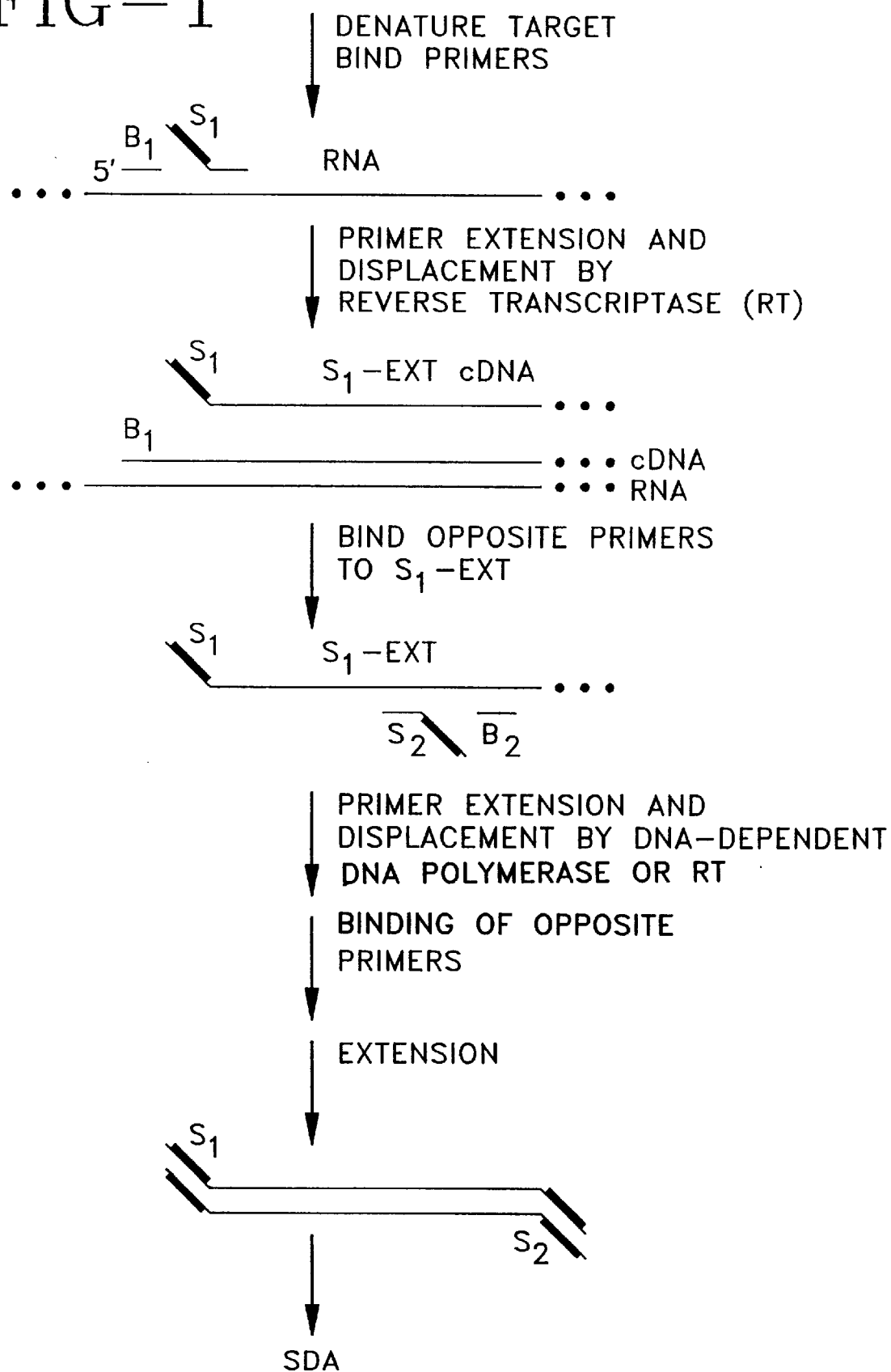

STRAND DISPLACEMENT AMPLIFICATION OF RNA TARGETS

This is a continuation-in-part of application Ser. No. 08/531,986, filed Sep. 21, 1995, now abandoned.

FIELD OF THE INVENTION

The present invention relates to amplification of nucleic acid target sequences and in particular to amplification of RNA target sequences.

BACKGROUND OF THE INVENTION

Nucleic acid amplification techniques have provided powerful tools for detection and analysis of small amounts of nucleic acids. The extreme sensitivity of such methods has lead to attempts to develop them for early diagnosis of infectious and genetic diseases, isolation of genes for analysis, and detection of specific nucleic acids in forensic medicine. Nucleic acid amplification techniques can be grouped according to the temperature requirements of the procedure. The polymerase chain reaction (PCR), ligase chain reaction (LCR) and transcription-based amplification require repeated cycling of the reaction between high and low temperatures to regenerate single stranded target molecules for subsequent cycles of amplification. In contrast, methods such as Strand Displacement Amplification (SDA), self-sustained sequence replication (3SR), Nucleic Acid Sequence Based Amplification (NASBA) and the Qβ replicase system are isothermal reactions which can be performed at a constant temperature.

In the PCR, the temperature of the reaction is raised after primer extension to separate the newly-synthesized strand from the template. The temperature is then lowered to reanneal the primers and repeat the extension process. The steps of the PCR reaction therefore occur in discrete phases or cycles as a result of the temperature constraints of the reaction. In contrast, in Strand Displacement Amplification (SDA) and other isothermal amplification reactions, extension of primers, displacement of single stranded extension products, annealing of primers to the extension products (or the original target sequence) and subsequent extension of the primers occur concurrently in the reaction mix. Conventional SDA (performed at lower temperatures, usually about 35–45° C.) is described by G. T. Walker, et al. (1992a. Proc. Natl. Acad. Sci. USA 89, 392–396 and 1992b. Nuc. Acids Res. 20, 1691–1696, U.S. Patents). A thermophilic version of the SDA reaction (tSDA) has recently been developed, and is performed at a higher, but still constant, temperature using thermostable polymerases and restriction endonucleases. tSDA has the advantage of increased specificity and a more rapid reaction time. The reaction is performed essentially as conventional SDA, with substitution of a thermostable polymerase and a thermostable restriction endonuclease. The temperature of the reaction is adjusted to a higher temperature suitable for the selected thermophilic enzymes (typically between about 45° C. and 60° C.) and the conventional restriction endonuclease recognition/cleavage site is replaced by the appropriate restriction endonuclease recognition/cleavage site for the selected thermostable endonuclease. Also in contrast to conventional SDA, the practitioner may include the enzymes in the reaction mixture prior to the initial heat denaturation step if they are sufficiently stable at that temperature.

Targets for amplification by SDA may be prepared by fragmenting larger nucleic acids using the endonuclease used in the SDA reaction. However, when the target is not flanked by the necessary restriction endonuclease recognition sites for fragmentation, target nucleic acids having appropriate restriction endonuclease recognition sites for nicking in the SDA reaction may be generated as described by Walker, et al. (1992b, supra and U.S. Pat. No. 5,270,184). As in SDA, the individual steps of the target generation reaction occur concurrently and continuously, generating targets with the terminal recognition sequences required for nicking by the restriction enzyme in SDA. As all of the components of the SDA reaction are present in the target generation reaction, generated targets automatically and continuously enter the SDA cycle and are amplified.

As the mRNA transcripts of an expressed gene are generally present in the cell in greater copy number than the gene itself, detection of RNA targets alone, or both RNA targets and DNA targets may overcome problems of inadequate sensitivity in some amplification reactions. Amplification of RNA and DNA targets is often desirable for diagnostic application of amplification technologies, as this gives the greatest number of amplifiable targets per sample, and, as a result, the greatest diagnostic sensitivity. Amplification of RNA targets is also useful for diagnostic monitoring of RNA-related conditions such as certain viremias, upregulation of cancer genes, etc. Amplification of RNA targets is referred to as "reverse transcription amplification," the best known method being reverse transcription PCR (rtPCR, J. W. Larrick. 1992. Trends Biotechnology 10, 146–152). rtPCR is often performed in sequential steps, the first being a reaction in which a reverse transcriptase is used to generate a cDNA copy of the RNA target sequence. Reverse transcriptase is then inactivated, and in the second step DNA polymerase is added and the cDNA is amplified in a conventional PCR reaction. This format is consistent with the PCR reaction itself, which occurs in discrete phases of temperature cycling. Recently, rtPCR has been performed using a single polymerase for both reverse transcription and DNA polymerization (EP 0 632 134 A2). It has been reported that thermostable DNA-dependent DNA polymerases such as Taq and Tth have significant reverse transcriptase activity (U.S. Pat. No. 5,322,770) when evaluated under reaction conditions appropriate for reverse transcription. These assays did not require that the DNA-dependent DNA polymerase displace the cDNA from the RNA template or incorporate modified dNTPs using an RNA template.

Reverse transcriptases (typically viral enzymes) are very active in producing cDNA using RNA as a template for replication. AMV reverse transcriptase has also been shown to incorporate thiolated dNTPs into the cDNA (P. A. Bartlett and F. Eckstein. 1982. J Biol. Chem. 257, 8879–8884), although it was not previously known whether other reverse transcriptases had this capability. Strand displacing activity has also been reported for certain reverse transcriptases, but it was not previously known whether these enzymes would strand displace a cDNA containing modified nucleotides from an RNA template, as is required for SDA.

The following terms are defined herein as follows:

An amplification primer is a primer for amplification of a target sequence by hybridization and extension of the primer. For SDA, the 3' end of the amplification primer is a target binding sequence which hybridizes at the 3' end of the target sequence. The amplification primer further comprises a recognition site for a restriction endonuclease 5' to the target binding sequence, generally near its 5' end. The restriction endonuclease recognition site is a nucleotide sequence recognized by a restriction endonuclease which will nick a double stranded recognition site for the restriction endonuclease when the recognition site is hemimodified, as described by Walker, et al. (1992a), supra. A hemimodified recognition site is a double stranded recognition site for a restriction endonuclease in which one strand contains at least one derivatized nucleotide which prevents cutting of one of the strands of the duplex by the restriction endonuclease. "Nicking" refers to this modified activity, in which only one strand of the duplex is cut by the restriction endonuclease, in contrast to typical double-stranded cleavage. Any hemimodified restriction endonuclease recognition site which is nickable by a restriction endonuclease is suitable for use in SDA. Amplification primers for SDA are designated $S_1$ and $S_2$ by Walker, et al. (1992b), supra. Alpha-thio modified deoxyribonucleoside triphosphates are abbreviated "dNTPαS," "dATPαS," "dCTPαS," etc.

The structure of amplification primers adapted for use in amplification reactions other than SDA is also known in the art. For example, as PCR does not require any specialized structure or sequence to sustain amplification, the PCR amplification primer typically contains only target binding sequences. However, the amplification primers of 3SR and NASBA contain an RNA polymerase promoter sequence in addition to the target binding sequences because a transcription step is required to sustain these amplification reactions.

A "bumper" or external primer is a primer which anneals to a target sequence upstream of (i.e., 5' to) an amplification primer, such that extension of the external primer displaces the downstream primer and its extension product, i.e., a copy of the target sequence comprising the restriction endonuclease recognition site is displaced. The bumper primers therefore consist only of target binding sequences and are designed so that they anneal upstream of the amplification primers and displace them when extended. External primers are designated $B_1$ and $B_2$ by Walker, et al. (1992b), supra. Extension of external primers is one method for displacing the extension products of amplification primers, but heating may also be suitable in certain cases.

A reverse transcription primer also consists only of target binding sequences. It is hybridized at the 3' end of an RNA target sequence to prime reverse transcription of the target. Extension of the reverse transcription primer produces a heteroduplex comprising the RNA target and the cDNA copy of the RNA target produced by reverse transcription. The cDNA is separated from the RNA strand (e.g., by heating, RNase H, or strand displacement) to make it single stranded and available for amplification. Optionally, a second reverse transcription primer may be hybridized at the 3' end of the target sequence in the cDNA to prime second strand synthesis prior to amplification.

The terms target or target sequence refer to nucleic acid sequences (DNA and/or RNA) to be amplified, replicated or detected. These include the original nucleic acid sequence to be amplified and its complementary second strand as well as either strand of a copy of the original target sequence produced by amplification or replication of the target sequence.

Amplification products, extension products or amplicons are oligonucleotides or polynucleotides which comprise copies of the target sequence produced during amplification or replication of the target sequence.

The term thermostable or thermophilic with reference to DNA-dependent DNA polymerases and other enzymes indicates that the enzymatic activity of the DNA polymerase or other enzyme is stable within the temperature range of tSDA, typically about 45° C.–60° C.

SUMMARY OF THE INVENTION

Strand Displacement Amplification has been adapted to reverse transcription amplification of RNA targets. The method of the invention is referred to as reverse transcription SDA (rtSDA) and may be performed as a two-step process or in a one-step process in which cDNA copies of an RNA target sequence are generated and amplified concurrently. Reverse transcriptase activity has been reported in thermophilic DNA-dependent DNA polymerases. However, it was found that the DNA polymerases preferred for use in thermophilic SDA (tSDA) do not produce detectable levels of cDNA under typical SDA reaction conditions. This initially appeared to preclude rtSDA as a one-step process, as a single DNA polymerase could not perform both the reverse transcription and DNA amplification steps. This problem has now been solved by adapting SDA reaction conditions such that a conventional reverse transcriptase and a DNA-dependent polymerase function together in a single reaction to produce cDNA and amplify it.

It was further discovered that the failure of rtSDA using only the DNA-dependent DNA polymerase under typical SDA reaction conditions was at least partially due to the inability of the polymerase to strand displace cDNA from the RNA template. In an alternative embodiment, this problem has been overcome by introducing a step between reverse transcription and amplification in which the cDNA is rendered single-stranded by separation from the RNA, e.g., by heating or enzymatic digestion of the RNA.

DESCRIPTION OF THE DRAWINGS

FIG. 1 illustrates the rtSDA reaction scheme for the two-polymerase/one-step embodiment of the invention.

DETAILED DESCRIPTION OF THE INVENTION

Thermostable DNA-dependent DNA polymerases were evaluated in a reverse transcription (RT) primer extension assay for their potential utility in rtSDA. In the RT primer extension assay, a cloned fragment of the HIV gag gene under control of a T7 promoter was transcribed in vitro to produce RNA targets. A reverse transcription primer which hybridized to the target region of the RNA was synthesized. The RNA target ($10^{10}$ molecules) and 160 nM kinased primer were denatured in either a phosphate reaction buffer (35 mM $KPO_4$, 0.2 mM dNTP, 15% glycerol, 0–4 mM $MgCl_2$, 0–4 mM $MnSO_4$) or a TRIS reaction buffer (10 mM TRIS, 50 mM KCl, 0.2 mM dNTPs, 15% glycerol, 0–4 mM $MgCl_2$ or $MnSO_4$) and equilibrated to 53° C. The reverse transcription reaction was initiated by addition of 11 U exo$^-$ Bca and incubated for 25 minutes. The reaction products were analyzed on polyacrylamide gels, using the predicted size of the extension product (238 nucleotides) to determine if the primer had been extended under the conditions of the reaction. Failure to extend the primer indicated that the polymerase had little or no reverse transcriptase activity.

PCR amplification of the primer extension products of the RT assay demonstrated that at high target levels ($10^{10}$ copies) neither exogenous magnesium or manganese were required for reverse transcription. At lower target levels ($\leq 10^4$ copies) reverse transcription required added magnesium in either buffer system. Manganese was required in TRIS buffer but apparently was not necessary in phosphate. However, it is possible that manganese was present in the phosphate buffer system as a component of another reagent, so a manganese requirement cannot be conclusively ruled out.

Exo⁻ Bst, exo⁻ Bca and Tth produced full length cDNA in the RT primer extension assay, whereas Taq did not. The exo⁻ Bst and exo⁻ Bca polymerases are commonly used in thermophilic SDA (tSDA). In general, exo⁻ Bca had somewhat reduced reverse transcriptase activity as compared to conventional reverse transcriptases but showed 100- to 1000-fold better reverse transcriptase activity than exo⁻ Bst. In contrast, at least fifty times the amount of exo⁻ Bst was needed to extend a DNA primer on an RNA template as compared to a conventional reverse transcriptase (Superscript II™). Although the DNA-dependent DNA polymerases were less active as reverse transcriptases than conventional reverse transcriptases, it was expected that they would be sufficiently active for use in rtSDA. When tested for reverse transcriptase activity under typical SDA reaction conditions, however, it was found that the DNA-dependent DNA polymerases supported little reverse transcription. Amplifying the reverse transcription products by PCR demonstrated a $10^9$ and $10^6$ molecule detection sensitivity for exo⁻ Bst and exo⁻ Bca, respectively. In contrast, reverse transcription using AMV reverse transcriptase with subsequent PCR amplification has demonstrated 100–1000 molecule detection sensitivity. Reduced sensitivity may be attributed to the reduced amounts of the polymerase in SDA as compared to the RT assay as well as possible inhibitory effects of the other components of the SDA reaction (e.g., modified dNTP, dUTP, primers, etc.).

Although detection levels were not sufficiently sensitive for clinical diagnostic assays, these experiments did demonstrate a low level of reverse transcription under these specific conditions. It was also observed that no amplification of the reverse transcription products was detectable in the absence of heating prior to amplification, indicating that the DNA-dependent DNA polymerase did not displace the cDNA strand from the RNA template. Essentially total failure to strand displace was found at lower concentrations of target RNA and only minimal strand displacement could be detected at high target concentrations. These investigations lead to the conclusion that exo- Bca and exo- Bst are substantially incapable of displacing extension products from the RNA template at clinically useful target concentrations.

In complete in vitro rtSDA reactions containing the typical SDA primers and reagents no amplification of RNA targets could be demonstrated using exo⁻ Bst or exo⁻ Bca as the only polymerase. In contrast, addition of Superscript™ reverse transcriptase to the exo⁻ Bca or exo⁻ Bst SDA reactions allowed efficient amplification of RNA targets. Further investigation suggested that the SDA amplification primers (those containing the nickable restriction site) inhibited reverse transcription by the DNA-dependent DNA polymerase. The presence of SDA primers coupled with the reduced efficiency of reverse transcription (especially at the relatively low concentrations of polymerase present in the SDA reaction) resulted in no detectable amplification regardless of whether or not the reaction was heated to denature double-stranded molecules between the reverse transcription and amplification steps. It was subsequently discovered that a detectable level of RNA target amplification could be achieved under typical SDA reaction conditions by substituting PCR-like or bumper-like reverse transcription primers for the specialized amplification primers required by SDA and heating the double-stranded heteroduplex reverse transcription products between reverse transcription and amplification of the cDNA.

These experiments indicated that amplification primers for SDA may inhibit reverse transcription by the DNA-dependent DNA polymerase and that the DNA-dependent DNA polymerase is substantially incapable of displacing cDNA from an RNA template at the relatively low target RNA concentrations which would be found in most clinical samples. Very low levels of strand displacement may occur at very high levels of target (about $10^{10}$ copies of RNA), but target concentrations this high are likely to be rare in clinical samples. Strand displacement is an essential feature of the conventional SDA reaction. To achieve efficient amplification of RNA targets using a single-polymerase system for rtSDA, it is therefore preferred that the reaction be performed in two separate steps. Only a single bumper-like primer (a reverse transcription primer) is present in the first reverse transcription step of the reaction. The cDNA is then separated from the RNA template prior to the second amplification step. In the first step, reverse transcription is performed by the DNA-dependent DNA polymerase in the presence of the reverse transcription primer. Reverse transcription primers are primers which do not contain the specialized sequences required by SDA, i.e., they contain only target binding sequences and are structurally similar to PCR amplification primers or the bumper primers of SDA. After reverse transcription (i.e., extension of the reverse transcription primer), the reaction is heated to denature the double-stranded RNA/cDNA hybrids or treated enzymatically to digest the RNA. SDA primers are then added and the amplification reaction is allowed to proceed in the presence of the same DNA-dependent DNA polymerase. Because the reverse transcription and amplification reactions occur in separate, discrete steps, this embodiment is referred to as the "one polymerase/two-step" method for rtSDA. Although amplification of RNA targets is generally detectable in the one polymerase/two-step method, it has the disadvantage of low sensitivity if polymerase concentrations are low. With increased concentrations of polymerase, however, a sensitivity of about 100–1000 RNA targets may be achieved.

In the reverse transcription step of the one-polymerase/two-step rtSDA reaction, reverse transcription of the RNA target by the DNA-dependent DNA polymerase is primed by hybridization and extension of a reverse transcription primer which consists only of target binding sequence, as SDA amplification primers may inhibit reverse transcription. The reverse transcription primer hybridizes upstream of the target to be amplified and may optionally be one of the bumper primers used in the second amplification step. The cDNA in the resulting cDNA/RNA heteroduplex is then rendered single-stranded by heating or enzymatic treatment (e.g., RNaseH), as the DNA polymerase does not displace the cDNA from the RNA template with sufficient efficiency. The cDNA thus produced does not have the appended terminal sequences necessary for SDA, but the amplification and bumper primers, when present in the subsequent amplification step, append these sequences according to the target generation scheme described by Walker, et al. (1992b, supra and U.S. Pat. No. 5,270,184). Appending the restriction endonuclease recognition site to the cDNA using the bumper and amplification primers in the DNA amplification step is generally preferable. Optionally, however, second strand synthesis may be performed prior to SDA by hybridization and extension of a second reverse transcription primer on the single-stranded cDNA. After separation of the two DNA target strands thus produced (typically by heating), only amplification primers for SDA (i.e., no bumper primers) are required for the DNA amplification step if the target binding sequences of the amplification primers correspond to the target binding sequences of the reverse transcription primers. In this embodiment, target generation and/or amplification occur in the SDA step, and the reverse transcription step simply provides a cDNA copy of the RNA target sequence. The two reaction steps are separated by an intervening step which renders the cDNA single-stranded. This is necessary because of the inability of the DNA polymerase to strand displace, although the DNA polymerase performs both the reverse transcription and amplification steps.

AMV, MMLV, Superscript II™, HIV-I and Retrotherm™ are conventional reverse transcriptases which were evaluated for SDA-related functions such as incorporation of dNTP αS and strand displacing activity. In this assay, amplification and bumper primers for SDA which hybridized to the HIV gag transcripts were designed and synthesized. The RNA target and an excess of kinased amplification and bumper primers were denatured in the buffer recommended by the manufacturer for use with the selected reverse transcriptase, and the reverse transcriptase was added after equilibrating the sample to the desired reaction temperature. Primers were hybridized and extended in the presence of dNTPs, at least one of which was dNTPαS. The reaction products were analyzed on polyacrylamide gels, using the predicted sizes of the extension products to determine which primers, if any had been extended under the conditions of the reaction. The expected sizes of the fully extended primer extension products were as follows: $S_{1ext}$–200 nucleotides, $B_{1ext}$–238 nucleotides, $S_{2ext}$–150 nucleotides, and $B_{2ext}$–190 nucleotides. Failure to extend the bumper primer which initially hybridized to the RNA indicated that the enzyme was incapable of displacing a primer hybridized downstream or that it could not incorporate dNTPαS. Failure to extend the first amplification primer (hybridized to the RNA downstream of the initial bumper primer) indicated either that the polymerase had no reverse transcriptase activity or that it was incapable of incorporating dNTPαS. Failure to extend the second amplification primer which hybridized to this cDNA (i.e., the extended single stranded first amplification primer extension product) indicated that the polymerase could not synthesize a second strand using the cDNA as a template or that it could not incorporate dNTPαS.

AMV, MMLV, Superscript II™, HIV-I and Retrotherm™ were tested in the reverse transcriptase assay. Of these, AMV, MMLV and Superscript II™ incorporated dNTPαS into cDNA. Superscript II™ was generally found to be the most active. Full length primer extension products were not detectable using HIV-I reverse transcriptase so no further studies were done to evaluate this enzyme. AMV, MMLV and Superscript II™ exhibited strand displacing activity, as evidenced by both $S_1$ and $B_1$ extension products ($S_{1ext}$ and $B_{1ext}$) in approximately equal amounts. Strand displacing activity was not detected for Retrotherm™, probably because of the 5'→3' exonuclease activity associated with this enzyme. However, strand displacing activity may be observed if the exonuclease activity is eliminated. Second strand synthesis (the ability to initiate polymerization on the cDNA produced by reverse transcription) was demonstrated for AMV using both radiolabled dNTPs and an end-labeled $S_2$ primer. Although second strand synthesis was not experimentally demonstrated for all of the reverse transcriptases tested, all have been reported to have this activity. Further, those with known RNase H activity should make both the $B_1$ extension product and the displaced $S_1$ extension product available for second strand synthesis. If the reverse transcriptase does not have intrinsic RNase H activity, RNase H can be added to the RT reaction when second strand synthesis is desired. However, second strand synthesis is not an essential feature, as the second strand can be synthesized by the DNA-dependent DNA polymerase in rtSDA.

To improve the efficiency of rtSDA for diagnostic use, the composition of the SDA reaction mixture was investigated in an attempt to take advantage of the high reverse transcriptase activity and strand displacing ability of the conventional reverse transcriptases as well as the high efficiency of the DNA-dependent DNA polymerases in DNA amplification. Preferably, such a reaction would allow both polymerases to be present and concurrently performing their respective functions in a "two-polymerase/one-step" reaction. As it appeared that the DNA-dependent DNA polymerase was unable to strand displace cDNA from the RNA template, reaction conditions compatible with DNA amplification which might allow the reverse transcriptase to perform this function were investigated. Preferably, the reverse transcriptase would reverse transcribe and strand displace the cDNA using the same SDA amplification and bumper primers employed in the DNA amplification portion of the reaction. Using these same SDA amplification primers, the DNA-dependent DNA polymerase would then amplify the displaced cDNAs as they were produced, without the need to introduce a denaturation step between the reverse transcription and amplification reactions. That is, the reverse transcription and cDNA amplification reactions would occur concurrently in a single reaction mixture.

The two-polymerase/one-step rtSDA reaction is diagrammed in FIG. 1. In the reverse transcription portion of the reaction, an amplification primer for SDA is hyridized to the RNA target sequence and a bumper primer is hybridized upstream of the amplification primer such that extension of the bumper primer displaces the extended amplification primer (the amplification primer extension product). This process is similar to the target generation reaction for SDA described in U.S. Pat. No. 5,270,184, except that the amplifiable target is generated from an RNA template using the reverse transcriptase for primer extension and strand displacement. The inability of the DNA-dependent DNA polymerase to strand displace from RNA prevents its participation in this portion of the two-polymerase/one-step rtSDA reaction. As the RNA is single stranded, only one SDA amplification primer and one bumper primer hybridize and are extended on the original RNA target. The opposite SDA amplification primer and bumper primer hybridize to, and are extended on, the cDNA produced by reverse transcription. Briefly, an amplification primer for SDA (e.g., $S_1$) hybridizes at the 3' end of the RNA target sequence. The bumper primer (e.g., $B_1$) hybridizes to the target sequence 5' (i.e., upstream) of $S_1$. The reverse transcriptase simultaneously extends both primers in the presence of deoxynucleoside triphosphates, at least one of which is a modified deoxynucleoside triphosphate, for example thiolated dATP (dATPαS) or thiolated dCTP (dCTPαS). The cDNA extension product of $S_1$ ($S_{1ext}$) is thereby displaced from the RNA template by the reverse transcriptase as $B_1$ is extended. The displaced, single stranded cDNA, now with an added restriction endonuclease recognition site at the 5' end, serves as a template for hybridization of the opposite SDA amplification primer ($S_2$) at the 3' end of the target sequence in the cDNA. The second bumper primer ($B_2$) hybridizes 5' to the $S_2$ amplification primer (i.e., $S_{1ext}$ binds $S_2$ and $B_2$). This may be a substrate for either the reverse transcriptase or the DNA-dependent DNA polymerase. Extension of $S_2$ and $B_2$ on the cDNA target by the reverse transcriptase or the DNA-dependent DNA polymerase (commonly referred to as "second strand synthesis") results in displacement of a single-stranded DNA extension product which corresponds to the original RNA target sequence, but with the restriction endonuclease recognition site appended to each end. This extension product is rendered double-stranded by hybridization and extension of $S_1$. Because polymerization occurs in the presence of at least one modified dNTP, the double-stranded restriction endonuclease recognition/cleavage sites at each end become hemimodified in this process. The double-stranded DNA structure is therefore a suitable substrate for amplification by SDA. Under ideal conditions in the one-step reaction, the individual steps of reverse transcription, target generation and amplification occur concurrently and continuously until all RNA targets have been reverse transcribed, then amplification of the cDNAs continues until the reaction is stopped. As they are generated, double-stranded DNA targets with the recognition/cleavage sequences at the ends automatically enter the SDA cycle and are amplified.

The SDA reaction medium (particularly the concentration of DNA-dependent DNA polymerase used in SDA) effectively prevents reverse transcription by the DNA polymerase. This is desirable because DNA polymerase-initiated reverse transcription reduces assay sensitivity, producing cDNAs which cannot be subsequently amplified due to the lack of strand displacement. In contrast, the reverse transcriptase efficiently reverse transcribes and strand displaces the cDNAs from the RNA templates. The DNA-dependent DNA polymerase efficiently amplifies these DNA targets in the conventional tSDA reaction as they are produced by reverse transcription. The term "one step" indicates the concurrent nature of the reverse transcription and amplification steps in this embodiment. Both MMLV and Superscript II™ reverse transcriptases produced efficient amplification when paired with either exo- Bca or Klenow DNA polymerases. Using exo⁻ Bca, Superscript II™ and BsoBI, rtSDA was capable of detecting as few as about 100 copies of gag RNA transcript. AMV reverse transcriptase with exo⁻ Bst and BsoBI also detected as few as about 100 gag RNA transcripts. Further routine optimization of the reaction should increase sensitivity. No RNA amplification was detectable when either the reverse transcriptase or the DNA-dependent DNA polymerase was omitted, confirming that neither polymerase alone was capable of performing the entire rtSDA reaction (reverse transcription and DNA amplification) in a one-step reaction format under these reaction conditions.

The foregoing description of the two-polymerase/one-step rtSDA reaction uses SDA amplification primers and bumper primers as an illustrative example. However, as the reverse transcriptase is capable of performing strand displacement with either SDA primers or reverse transcription primers, reverse transcription primers may be additionally present for use by the reverse transcriptase in the reverse transcription portion of the reaction. The downstream reverse transcription primer functions as a reverse transcription primer and the upstream reverse transcription primer is similar to an SDA bumper primer, as its extension serves to displace the downstream reverse transcription primer extension product (the cDNA).

Following target amplification, the amplicons produced may be detected by any of the methods known in the art for detection of specific nucleic acid sequences. For example, amplification products may be detected by specific hybridization to an oligonucleotide detector probe. The detector probe is a short oligonucleotide which includes a detectable label, i.e., a moiety which generates or can be made to generate a detectable signal. The label may be incorporated into the oligonucleotide probe by nick translation, end-labeling or during chemical synthesis of the probe. Many directly and indirectly detectable labels are known in the art for use with oligonucleotide probes. Directly detectable labels include those labels which do not require further reaction to be made detectable, e.g., radioisotopes, fluorescent moieties and dyes. Indirectly detectable labels include those labels which must be reacted with additional reagents to be made detectable, e.g., enzymes capable of producing a colored reaction product (e.g., alkaline phosphatase or horseradish peroxidase), biotin, avidin, digoxigenin, antigens, haptens or fluorochromes. The signal from enzyme labels is generally developed by reacting the enzyme with its substrate and any additional reagents required to generate a colored enzymatic reaction product. Biotin (or avidin) labels may be detected by binding to labeled avidin (or labeled biotin) or labeled anti-biotin (or labeled anti-avidin) antibodies. Digoxigenin and hapten labels are usually detected by specific binding to a labeled anti-digoxigenin (anti-dig) or anti-hapten antibody. In general, the detector probe will be selected such that it hybridizes to a nucleotide sequence in the amplicon which is between the binding sites of the two amplification primers. However, a detector probe may also have the same nucleotide sequence as either of the amplification primers. Methods for detection in vitro and in situ by hybridization to a detector probe are known in the art.

Alternatively, amplification products may be detected by extension of a detector primer as described by Walker, et al. (1992b), supra. In the detector primer extension method an oligonucleotide primer comprising a detectable label is hybridized to the amplification products and extended by addition of polymerase. For detection the primer may be 5' end-labeled, for example using $^{32}P$ or a fluorescent label. Alternatively, extension of the hybridized primer may incorporate a dNTP analog comprising a directly or indirectly detectable label. For example, extension of the primer may incorporate a dig-derivatized dNTP, which is then detected after extension by reaction with AP-α-dig and a suitable AP substrate. The primer to be extended may either be the same as an amplification primer or it may be a different primer which hybridizes to a nucleotide sequence in the amplicon which is between the binding sites of the amplification primers.

The detectable label may also be incorporated directly into amplicons during target sequence amplification. For example, one of the dNTPs in the conventional SDA reaction may be completely or partially replaced with a dNTP analog which comprises a dNTP conjugated to a directly or indirectly detectable label. The polymerase then incorporates the label into the amplification products generated by extension of the amplification primer. The label may be directly or indirectly detectable. When the label conjugated to the dNTP is a fluorescent label which may be detected directly in the amplicons by measuring fluorescence intensity or it may be detected in situ by fluorescence microscopy or flow cytometry. When the label conjugated to the dNTP is biotin or digoxigenin, amplicons may be indirectly detected by reaction of the biotin or digoxigenin label with streptavidin/FITC and detection as for a directly linked fluorescent label.

Secondary amplification products are copies of the target sequence generated by hybridization and extension of a signal primer on the target sequence, as described in U.S. Pat. No. 5,547,861. The secondary amplification products comprise an internal segment of the amplified target sequence and a detectable label which is associated with the signal primer. At least the 3' end of the signal primer comprises a sequence which hybridizes to the target sequence. It may also include features which facilitate capture or immobilization of the secondary amplification products, so that they may be isolated for detection, quantitation or further manipulation. The signal primer does not comprise the restriction endonuclease recognition site found in the amplification primers and therefore does not function as an amplification primer in SDA. Concurrent generation of secondary amplification products in the rtSDA reaction provides another detection method which is homogeneous and may be performed concurrently with amplification. The probe hybridization step is eliminated, and concentrations of signal primer are generally lower than for hybridization probes. The lower concentration itself reduces background and also allows higher stringency washing which further reduces background. To generate secondary amplification products, at least one signal primer is included in the rtSDA reaction mixture. In two-step rtSDA, the signal primer may be present in both reactions or only in the cDNA amplification reaction. The signal primer(s) hybridizes to the RNA target sequence or a cDNA copy thereof downstream of the hybridization site of an amplification primer and is extended by polymerase in a manner similar to extension of the amplification primer. Extension of the amplification primer thereby displaces the extension product of the signal primer from the target sequence. The opposite amplification primer then hybridizes to the extended, displaced signal primer and is extended by polymerase, resulting in incorporation of the signal primer into a longer duplex indicative of target amplification (the secondary amplification product). In situ, remaining unextended signal primers are small enough to be washed out of the cell, whereas the extended signal primers are retained within it. Target amplification-specific signal thereby becomes associated with the cells where the target is present and is substantially absent from cells where there is no target.

In addition to the signal primer, other alternatives, modifications and adaptations of the SDA reaction for DNA are suitable for use in SDA of RNA targets. For example, single-strand DNA binding proteins may be added to the RNA amplification reaction to improve overall efficiency and increase the length of the target which may be efficiently amplified. Contaminating amplicons may be treated as taught in U.S. Pat. No. 5,536,649 to render them unamplifiable in the subsequent RNA amplification reaction and any of the restriction enzymes and polymerases used for SDA of DNA targets may be used in the RNA amplification reaction (e.g., the enzymes disclosed in U.S. Pat. No. 5,270,184; U.S. Pat. No. 5,455,166; EP 0684 315). Further, both the one-step and two-step protocols described above may be applied to in vitro amplification of RNA targets, as exemplified above, or to in situ amplification of RNA targets.

The following experimental examples are provided to illustrate certain embodiments of the invention, but are not intended to limit the invention as defined by the appended claims.

EXAMPLE 1 rtSDA was performed in one step using a reverse transcriptase and a DNA-dependent DNA polymerase to concurrently perform the reverse transcription and DNA amplification portions of the reaction. This reaction may be conducted in any appropriate SDA buffer system using any DNA-dependent DNA polymerase suitable for SDA of DNA targets. Thermophilic (i.e., thermostable) DNA polymerases are preferred (e.g., exo⁻ Bca or exo⁻ Bst) as they allow the reaction to be conducted under more stringent conditions. Any reverse transcriptase which strand displaces may be employed, the preferred reverse transcriptases being MMLV, AMV and Superscript II™. In a first example, the buffer system was based on TRIS and contained the following components: 100 μg/mL BSA, 50 mM TRIS pH 8.3, 75 mM KCl, 3 mM MgCl₂, 0.2 mM dATP, 0.2 mM dGTP, 0.2 mM dTTP, 1.4 mM dCTPαS, 450 ng human placenta DNA, 15% glycerol, 1.2 μM SDA amplification primers, and 0.5 μM SDA bumper primers (shown below, restriction endonuclease recognition sequences underlined) in a total volume of 50 μL.

Amplification Primer S1.8 (SEQ ID NO:1)
ACCGCATCGAATGCATGT<u>CTCGGG</u>TGGTAAAAGTAGTAGAAG Amplification Primer S2.9 (SEQ ID NO:2)
CGATTCCGCTCCAGACTT<u>CTCGGG</u>GTGTTTAGCATGGTGTT Bumper Primer GB1.1 (SEQ ID NO:3)
GTACTACAGGCCATATC Bumper Primer B2.1 (SEQ ID NO:4)
GCAGCTTCCTCATTG Detector primer (SEQ ID NO:5)
GGTGGCTCCTTCTGATAATG To determine the sensitivity of the assay, gag RNA target was diluted at various concentrations into the reaction mixture, heated to 70° C. for 30 seconds, and placed at 48° C. for two minutes. The amplification enzymes (BsoBI, reverse transcriptase and DNA polymerase) were added and the reaction was incubated for 30 minutes at about 48–52° C. In one example, 160 units BsoBI, 3 units exo⁻ Bca and either 200 units Superscript II™ or 2.5 units AMV reverse transcriptase were present in the amplification reaction. Upon completion of the amplification reaction, the amplification products were detected by hybridization and extension of a labeled detector primer as described by Walker, et al., 1992b, supra. In the TRIS system, rtSDA detected a minimum of about 100 copies of RNA.

The rtSDA reaction may also be conducted in phosphate buffers, which are the buffer systems typically used for SDA of DNA targets. These reactions contained the following components: 45 mM KPO₄ (pH 7.6), 5 mM MgOAC, 15% glycerol, 500 ng human placental DNA, 1.2 μM SDA amplification primers, 0.5 μM SDA bumper primers, 1.4 mM dCTPαS, 0.2 mM dATP, 0.2 mM dGTP, 0.2 mM dTTP, 100 μg/reaction BSA, and 160 units BsoBI in a 50 μL reaction. Exo⁻ Bca (3 units), exo⁻ Bst (16 units) and Klenow (15 units) were tested and found to be functional in the phosphate-based rtSDA reaction. AMV (2.5 units), Superscript II™ (200 units) and MMLV (200 units) reverse transcriptases were also tested and found to be compatible with the phosphate system. The most sensitive assay was achieved using AMV and exo⁻ Bst as the two polymerases, detecting a minimum of about 100 RNA target molecules.

It was confirmed that the one-step/two polymerase rtSDA system requires both polymerases for detectable amplification of RNA. Omission of either the reverse transcriptase or the DNA polymerase prevented amplification of gag RNA targets regardless of the buffer employed. The discovery that both the reverse transcriptase and the DNA polymerase can function concurrently under the same reaction conditions allowed development of an rtSDA reaction which requires fewer manipulations and can provide real-time detection of amplification products (i.e., detection simultaneously with amplification) using signal primer detection systems.

EXAMPLE 2 rtSDA was performed in a one-polymerase/two-step format using RNA target sequences transcribed by RNA polymerase from the cloned gag gene fragment as described above. In the first step, reverse transcription was performed by hybridization and extension of the $B_1$ bumper primer using 7.5 U/μL exo⁻ Bst or 0.15 U/μL exo⁻ Bca polymerase in 50 mM TRIS (pH 8.3), 75 mM KCl, 3 mM $MgCl_2$, 0.75 mM $MnSO_4$ or $MnCl_2$, 200 μM each dGTP, dATP and dTTP, and 1.4 mM dCTPαS. Alternatively, the reverse transcription reaction was performed in $KPO_4$ buffer used for the SDA step. Primer extension was allowed to continue for 1 hr. at 50° C. The reverse transcription reaction was then diluted for amplification in 35 mM $KPO_4$, 4 mM MgOAc, 200 μM each dGTP, dATP and dTTP, 1.4 mM dCTPαS, 500 nM amplification primers, 50 nM bumper primers, 15% glycerol and 10 ng/μL human DNA. The cDNA target was boiled for 2 min. in the SDA buffer, then equilibrated to 55° C. Eleven units of exo⁻ Bca or 16 units of exo⁻ Bst were added with 160 units of BsoBI. The amplification reaction was incubated for 15–30 min. at 55° C. Amplification products were detected in an aliquot of the completed reaction by hybridization and extension of the $^{32}$P-labeled detector primer as described by Walker, et al. (1992b, supra), adding an additional 11 units of exo⁻ Bca or exo⁻ Bst. An aliquot of the detector primer extension reaction was analyzed on an 8% polyacrylamide gel. The expected sizes of the detector primer extension products were 82 and 101 nucleotides.

The sample to which no cloned gag gene had been added and the DNase treated sample to which no RNA polymerase was added showed no detectable amplification products. Similarly, when the sample was treated with both DNase and RNase following transcription, no amplification products were seen. The sample in which RNA transcripts had been digested with RNase showed strong bands indicating that the gag DNA target had been amplified. When the sample was treated with DNase prior to reverse transcription, strong bands were also seen on the gel, demonstrating reverse transcription and specific amplification of RNA targets by rtSDA. Under the conditions of this experiment, the efficiency of amplification by rtSDA is approximately equal to the efficiency of SDA for DNA targets. Sensitivity was 100–1000 transcripts. This level of target was easily detected even though the reaction conditions were not rigorously optimized. Optimization of reaction conditions should improve sensitivity and allow detection of significantly fewer RNA target molecules.

Attempts to reproduce the one-polymerase/two step reaction with all of the typical SDA primers (amplification primers and bumpers) present during the reverse transcription step failed to produce any detectable amplification. This is attributed to the presence of the SDA amplification primers, as bumper primers successfully primed reverse transcription in the previous experiment. The SDA amplification primers may strongly inhibit cDNA generation by the DNA-dependent DNA polymerase, particularly under the conditions of SDA where reverse transcriptase activity is already suppressed. Alternatively, the formation of background amplification primer dimers during inefficient reverse transcription may out-compete the subsequent amplification reaction. Although this appears to be a common problem, it may not be the case for all amplification primer sets. The problem was overcome here by using reverse transcription primers for the reverse transcription step. However, different DNA-dependent DNA polymerases may be more efficient at reverse transcription in rtSDA when SDA amplification primers are present, overcoming the necessity of using reverse transcription primers.

What is claimed is:

1. A method for amplifying a target sequence comprising:
a) hybridizing a first amplification primer at a 3' end of an RNA target sequence, the first amplification primer comprising a restriction endonuclease recognition site 5' to a first target binding sequence, and hybridizing a first bumper primer 5' to the first amplification primer;
b) in the presence of deoxynucleoside triphosphates and at least one modified deoxynucleoside triphosphate, extending the first amplification primer and the first bumper primer using a reverse transcriptase which lacks 5'→3' exonuclease activity and has strand displacing activity, thereby producing a single-stranded first amplification primer extension product which comprises a DNA target sequence complementary to the RNA target sequence;
c) hybridizing a second amplification primer at a 3' end of the DNA target sequence of the first amplification primer extension product, the second amplification primer comprising the restriction endonuclease recognition site 5' to a second target binding sequence, and hybridizing a second bumper primer 5' to the second amplification primer;
d) extending the second amplification primer and the second bumper primer in the presence of the deoxynucleoside triphosphates and the modified deoxynucleoside triphosphate, thereby producing a single-stranded second amplification primer extension product comprising the DNA target sequence;
e) rendering the second amplification primer extension product double stranded by hybridization and extension of the first amplification primer, thereby producing a double stranded hemimodified restriction endonuclease recognition site in the double-stranded second amplification primer extension product, and;
f) amplifying the target sequence by i) nicking the double-stranded hemimodified restriction endonuclease recognition site in the double-stranded second amplification primer extension product with a restriction endonuclease,
ii) extending from the nick using a thermostable DNA-dependent DNA polymerase which lacks 5'→3' exonuclease activity and has strand displacing activity, thereby displacing a single stranded copy of the target sequence, and
iii) repeating the nicking, extending and displacing steps such that the target sequence is amplified.

2. The method of claim 1 wherein the DNA-dependent DNA polymerase is selected from the group consisting of exo⁻ Bca and exo⁻ Bst, and the reverse transcriptase is selected from the group consisting of Superscript II™, AMV reverse transcriptase and MMLV reverse transcriptase.

3. The method of claim 2 wherein the restriction endonuclease is BsoBI.

4. The method of claim 1 wherein the second amplification primer is extended by the reverse transcriptase.

5. The method of claim 1 wherein the second amplification primer is extended by the DNA-dependent DNA polymerase.

6. The method of claim 1 further comprising detecting the amplified target sequence.

7. The method of claim 6 wherein the amplified target sequence is detected by hybridization of a detector probe, extension of a detector primer, incorporation of a detectable label into an amplicon or generation of secondary amplification products.

8. The method of claim 6 wherein the target sequence is amplified and detected in situ.

9. A method for amplifying a target sequence comprising:
a) hybridizing a reverse transcription primer at a 3' end of an RNA target sequence and hybridizing a first bumper primer 5' to the reverse transcription primer;
b) in the presence of deoxynucleoside triphosphates, and at least one modified deoxynucleoside triphosphate, extending the reverse transcription primer and the first bumper primer using a reverse transcriptase which lacks 5'→3' exonuclease activity and has strand displacing activity, thereby producing a single-stranded reverse transcription primer extension product which comprises a DNA target sequence complementary to the RNA target sequence;

c) hybridizing a first amplification primer at a 3' end of the DNA target sequence, the first amplification primer comprising a restriction endonuclease recognition site 5' to a target binding sequence, and hybridizing a second bumper primer 5' to the first amplification primer;

d) extending the first amplification primer and the second bumper primer in the presence of the deoxynucleoside triphosphates and the modified deoxynucleoside triphosphate, thereby producing a single-stranded first amplification primer extension product comprising the DNA target sequence;

e) rendering the first amplification primer extension product double-stranded by hybridization and extension of a second amplification primer, the second amplification primer comprising the restriction endonuclease recognition site 5' to a second target binding sequence, thereby producing a double-stranded hemimodified restriction endonuclease recognition site in the double-stranded first amplification primer extension product, and;

f) amplifying the target sequence by
  i) nicking the double-stranded hemimodified restriction endonuclease recognition site in the double-stranded first amplification primer extension product with a restriction endonuclease,
  ii) extending from the nick using a thermostable DNA-dependent DNA polymerase which lacks 5'→3' exonuclease activity and has strand displacing activity, thereby displacing a single-stranded copy of the target sequence, and
  iii) repeating the nicking, extending and displacing steps such that the target sequence is amplified.

10. The method of claim 9 wherein the DNA-dependent DNA polymerase is selected from the group consisting of exo⁻ Bca and exo⁻ Bst, and the reverse transcriptase is selected from the group consisting of Superscript II™, AMV reverse transcriptase and MMLV reverse transcriptase.

11. The method of claim 10 wherein the restriction endonuclease is BsoBI.

12. The method of claim 9 wherein the first amplification primer is extended by the reverse transcriptase.

13. The method of claim 9 wherein the first amplification primer is extended by the DNA-dependent DNA polymerase.

14. The method of claim 9 further comprising detecting the amplified target sequence.

15. The method of claim 14 wherein the amplified target sequence is detected by hybridization of a detector probe, extension of a detector primer, incorporation of a detectable label into an amplicon or generation of secondary amplification products.

16. The method of claim 14 wherein the target sequence is amplified and detected in situ.

17. A method for amplifying a target sequence comprising:
  a) hybridizing a reverse transcription primer at a 3' end of an RNA target sequence, the reverse transcription primer consisting of a target binding sequence;
  b) in the presence of deoxynucleoside triphosphates and at least one modified deoxynucleoside triphosphate, extending the hybridized reverse transcription primer using a thermostable DNA-dependent DNA polymerase which lacks 5'→3' exonuclease activity, thereby producing a double-stranded RNA/DNA hybrid comprising a cDNA which is complementary to the RNA target sequence;
  c) rendering the cDNA single stranded by heat or enzymatic treatment;
  d) adding amplification primers and bumper primers for Strand Displacement Amplification, and;
  e) amplifying the single-stranded cDNA in a Strand Displacement Amplification reaction.

18. The method of claim 17 wherein the cDNA is rendered single-stranded by heating.

19. The method of claim 17 wherein the cDNA is rendered single-stranded by treatment with RNase H.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:1:

ACCGCATCGA ATGCATGTCT CGGGTGGTAA AAGTAGTAGA AG                    42

(2) INFORMATION FOR SEQ ID NO:2:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:2:

CGATTCCGCT CCAGACTTCT CGGGGTGTTT AGCATGGTGT T                     41

(2) INFORMATION FOR SEQ ID NO:3:

(i) SEQUENCE CHARACTERISTICS:
        (A) LENGTH: 17 base pairs

-continued

```
        (B) TYPE: nucleic acid
        (C) STRANDEDNESS: single
        (D) TOPOLOGY: linear (xi) SEQUENCE DESCRIPTION: SEQ ID NO:3:

GTACTACAGG CCATATC                                                        17

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:4:

GCAGCTTCCT CATTG                                                          15

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:5:

GGTGGCTCCT TCTGATAATG                                                     20
```